US010071106B2

(12) United States Patent
Marco Contelles et al.

(10) Patent No.: US 10,071,106 B2
(45) Date of Patent: Sep. 11, 2018

(54) STEROIDAL NITRONES FOR THE TREATMENT AND PREVENTION OF A CEREBRAL STROKE OR ISCHAEMIA, ALZHEIMER AND PARKINSON DISEASE AND AMYOTROPHIC LATERAL SCLEROSIS

(71) Applicant: FUNDACIÓN PARA LA INVESTIGACIÓN BIOMÉDICA DEL HOSPITAL UNIVERSITARIO RAMÓN Y CAJAL, Madrid (ES)

(72) Inventors: José Luis Marco Contelles, Madrid (ES); Alberto Alcázar González, Madrid (ES)

(73) Assignee: FUNDACIÓN PARA LA INVESTIGACIÓN BIOMÉDICA DEL HOSPITAL UNIVERSITARIO RAMÓN Y CAJAL, Madrid (ES)

( * ) Notice: Subject to any disclaimer, the term of this patent is extended or adjusted under 35 U.S.C. 154(b) by 0 days.

(21) Appl. No.: 14/892,755

(22) PCT Filed: May 22, 2014

(86) PCT No.: PCT/ES2014/070421
§ 371 (c)(1),
(2) Date: Nov. 20, 2015

(87) PCT Pub. No.: WO2014/188046
PCT Pub. Date: Nov. 27, 2014

(65) Prior Publication Data
US 2016/0089382 A1    Mar. 31, 2016

(30) Foreign Application Priority Data

May 22, 2013   (ES) .................................. 201330738

(51) Int. Cl.
| *A61K 31/575* | (2006.01) |
| *A61K 38/48* | (2006.01) |
| *G01N 33/50* | (2006.01) |
| *A61K 45/06* | (2006.01) |

(52) U.S. Cl.
CPC .......... *A61K 31/575* (2013.01); *A61K 38/482* (2013.01); *A61K 45/06* (2013.01); *G01N 33/502* (2013.01); *G01N 33/5058* (2013.01); *C12Y 304/21068* (2013.01)

(58) Field of Classification Search
CPC .............. A61K 31/575; A61K 2300/00; A61K 38/482; A61K 45/06; C12Y 304/21068; G01N 33/502; G01N 33/5058
See application file for complete search history.

(56) References Cited

FOREIGN PATENT DOCUMENTS

WO    WO-2013/017715 A2    2/2013

OTHER PUBLICATIONS

Bundgaard, Design of Prodrugs, 1985, chapter 1.*
Silverman (Prodrugs and Drug Delivery Systems, The Organic Chemistry of Drug Design and Drug Action, pp. 352-399, 1992.*
Banker, Prodrugs, Modern Pharmaceutics, Third Edition and Expanded, pp. 451 and 596 (1996).*
Wolff (Burger's Medicinal Chemistry and Drug Discovery, 5th Edition, vol. I Principles and Practice, pp. 975-977, 1995).*
A.M. Rouhi, Chem. & Eng. News, Feb. 24, 2003, 81(8), 32-35.*
Morissette et al. Adv. Drug Delivery Rev. 2004, 56,275-300.*
Matthew L. Peterson et. al., Journal of Pharmacy & Pharmaceutical Science 2006 (9(3):317-326.*
Korczyn et al. (Expert Rev. Neurother. 15(3), 2015).*
Arce, C. et al., "Drugs for stroke: Action of nitrone (Z)-N(2-bromo-5-hydroxy-4-methoxybenzylidene)-2-methylpropan-2-amine oxide on rat cortical neurons in culture subjected to oxygen-glucose-deprivation," *European Journal of Medicinal Chemistry*, vol. 55, pp. 475-479, 2012.
Green, A. et al., "Nitrones as neuroprotective agents in cerebral ischemia, with particular reference to NXY-059," *Pharmacology & Therapeutics*, vol. 100, pp. 195-214, 2003.
International Search Report and Written Opinion for PCT/ES2014/070421, dated Sep. 17, 2014.
Samadi, A. et al., "Synthesis, structure, theoretical and experimental in vitro antioxidant/pharmacological properties of aplha-aryl, N-alkyl nitrones, as potential agents for the treatment of cerebral ischemia," *Bioorganic & Medicinal Chemistry*, vol. 19, pp. 951-960, 2011.

* cited by examiner

*Primary Examiner* — Umamaheswari Ramachandran
(74) *Attorney, Agent, or Firm* — Squire Patton Boggs (US) LLP

(57) ABSTRACT

The invention relates to neuroprotective, antioxidant steroidal nitrones to which the blood-brain barrier is highly permeable, as potential drugs for the treatment of a cerebral stroke or ischaemia, Alzheimer and Parkinson disease and amyotrophic lateral sclerosis.

14 Claims, 5 Drawing Sheets

STEROIDAL NITRONES FOR THE TREATMENT AND PREVENTION OF A CEREBRAL STROKE OR ISCHAEMIA, ALZHEIMER AND PARKINSON DISEASE AND AMYOTROPHIC LATERAL SCLEROSIS

RELATED APPLICATIONS

This application is a 35 U.S.C. § 371 national stage filing of International Application No. PCT/ES2014/070421, filed on May 22, 2014, which claims priority to Spanish Patent Application No. P201330738, filed on May 22, 2013. The entire contents of each of the foregoing applications are incorporated herein by reference.

TECHNICAL FIELD

The present invention relates to the medical field, particularly to the use of steroidal nitrones for the treatment and prevention of a cerebral stroke or ischaemia, Alzheimer's and Parkinson's disease and amyotrophic lateral sclerosis.

PRIOR ART

It is known that lipid cell membrane oxidation is one of the most important pharmacological events taking place during a stroke, which leads and translates into the death of brain tissue and neurons (Brouns, R.; De Deyn, P. P. The complexity of neurobiological processes in acute ischemic stroke. Clin. Neurol. Neurosurg. 2009, 111, 483-495). Accordingly, one of the most active research areas for the treatment of strokes focuses on searching for new permeable agents with a strong antioxidant capacity and strong neuroprotective action that are able to block the various types of oxygen free radicals (ROS), responsible for the oxidative stress caused by the stroke, a serious and rapidly growing pathology in advanced societies for which there is no efficient treatment, and which is the fourth cause of death after cancer, coronary heart disease and Alzheimer's disease (Chan, P. H. The role of oxygen radicals in brain injury and edema, in Chow C K (ed): Cellular Antioxidant Defense Mechanisms, Volume III. Boca Raton, Fla., CRC Press, Inc, 1988, pp. 89-109). In fact, the neuron membrane is rich in polyunsaturated fatty acids, which are particularly sensitive to the action of hydroxyl-, peroxyl-, and superoxide-type ROSs in positions adjacent to double bonds, generating very reactive allyl radicals capable of producing new radical chain reactions, i.e., new, more complex radicals, or interacting with metals, such as iron, to generate new, even more toxic and harmful radicals.

For that reason the strategy used against stroke based on the development of ROS trapping and blocking agents is an area of permanent interest and research.

It is in this context where nitrone-type organic compounds have played a key role in the last thirty years given their structure and properties, but unfortunately their supposed beneficial activity in a number of clinical trials to which a wide range of said compounds have been subjected is far from being corroborated (Floyd, R. A.; Kopke, R. D. Choi, C. H.; Foster, S. B.; Doblas, S.; Towner, R. A. Nitrones as therapeutics. Free Radic. Biol. Med. 2008, 45, 1361-1374).

In that sense, (Z)-α-phenyl-N-tert-butylnitrone (PBN) inhibits lipoprotein oxidation (Kalyanaraman, B.; Joseph, J.; Parthasarathy, S. The spin trap, α-phenyl N-tert-butylnitrone, inhibits the oxidative modification of low density lipoprotein FEBS Lett. 1991, 280, 17-20), reduces oxidative damage in red blood cells, lipid peroxidation due to phenylhydrazine (Hill, H. A.; Thornalley, P. J. The effect of spin traps on phenylhydrazine-induced haemolysis. Biochim. Biophys. Acta 1983, 762, 44-51), and protects rats from ischaemia and from MPTP toxicity (Margaill, I.; Plotkine, M.; Lerouet, D. Antioxidant strategies in the treatment of stroke. Free. Radic. Biol. Med. 2005, 39, 429-443).

Nitrone NXY-059 (Kuroda, S.; Tsuchidate, R.; Smith, M. L.; Maples, K. R.; Siesjo, B. K. Neuroprotective effects of a novel nitrone, NXY-059, after transient focal cerebral ischaemia in the rat. J. Cereb. Blood Flow Metab. 1999, 19, 778-787) is an excellent neuroprotective ROS trap, but it has failed repeatedly in clinical trials (Macleod, M. R.; van der Worp, H. B.; Sena, E. S.; Howells, D. W.; Dirnagl, U.; Donnan, G. A. Evidence for the efficacy of NXY-059 in experimental focal cerebral ischaemia is confounded by study quality. Stroke 2008, 39, 2824-2829).

Nevertheless, efforts to find the optimal nitrone have not ceased [(a) Goldstein, S.; P. Lestage, P. Chemical and pharmacological aspects of heteroaryl-nitrones. Curr. Med. Chem. 2000, 7, 1255-1267; (b) Dias, A. G.; Santos, C. E.; Cyrino, F. Z.; Bouskela, E.; Costa, P. R. N-tert-Butyl and N-methyl nitrones derived from aromatic aldehydes inhibit macromolecular permeability increase induced by ischemia/reperfusion in hamsters. Bioorg. Med. Chem. 2009, 17, 3995-3998; (c) Porcal, W.; P. Hernández, P.; González, M.; Ferreira, A.; Olea-Azar, C.; Cerecetto, H.; Castro, A. Heteroarylnitrones as drugs for neurodegenerative diseases: Synthesis, neuroprotective properties, and free radical scavenger properties. J. Med. Chem. 2008, 51, 6150-6159; (d) Kim, S.; Bouajila, J.; Dias, A. G.; Cyrino, F. Z.; Bouskela, E.; Costa, P. R.; Nepveu, F. α-Phenyl-N-tert-butyl nitrone (PBN) derivatives: Synthesis and protective action against microvascular damages induced by ischemia/reperfusion. Bioorg. Med. Chem. 2007, 15, 3572-3578; (e) Balogh, G. T.; Vukics, K.; Konczol, A.; Kis-Varga, A.; Gere, A.; Fischer, J. Nitrone derivatives of trolox as neuroprotective agents. Bioorg. Med. Chem. Lett. 2005, 15, 3012-3015; (f) Becker, D. A.; Ley, J. J.; Echegoyen, L.; Alvarado, R. Stilbazulenyl nitrone (STAZN): A nitronyl-substituted hydrocarbon with the potency of classical phenolic chain-breaking antioxidants. J. Am. Chem. Soc. 2002, 124, 4678-4684; (g) Dhainaut, A.; Tizot, A.; Raimbaud, E.; Lockhart, B.; Lestage, P.; Goldstein, S. Synthesis, structure, and neuroprotective properties of novel imidazolyl nitrones. J. Med. Chem. 2000, 43, 2165-2175].

On the other hand, steroids are organic compounds having a recognized biological activity, among which their capacity for acting as neuroprotective agents in inflammatory processes affecting the central nervous system stand out and translate into neurological diseases, such as cerebral ischaemia, Alzheimer's and Parkinson's disease and amyotrophic lateral sclerosis.

DESCRIPTION OF THE INVENTION

Figure 1:
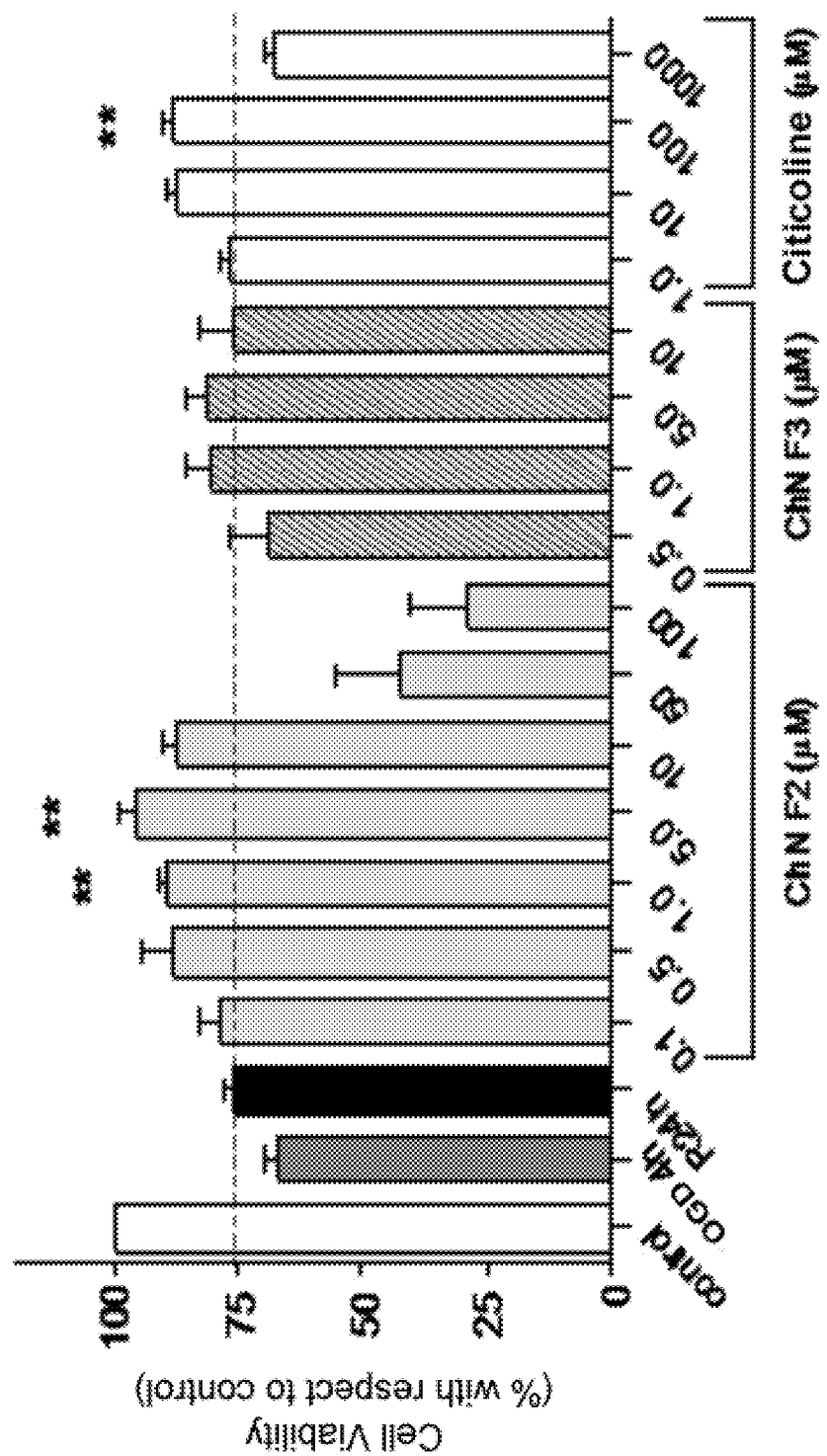
FIG. 1 shows how the addition of cholesteronitrone F2 at 1 or 5 µM, but not cholesteronitrone F3, significantly increased neuronal viability during reperfusion, and the control value (89.1 and 95.5%, for cholesteronitrone F2 at 1 or 5 µM, respectively; ANOVA, p<0.0001; and p<0.01, post-Dunnett test compared with R24h) was almost reached at the 5 µM concentration.

In the context of recent research aimed at the synthesis and biological evaluation of new nitrones for the treatment of strokes [(a) Abdelouahid, S.; Soriano, E.; Revuelta, J.; Valderas, C.; Chioua, M.; Garrido, I.; Bartolomé, B.; Tomas-solli, I.; Ismaili, L.; González-Lafuente, L.; Villarroya, M.; García, A. G.; Oset-Gasque M. J.; Marco-Contelles, J. Synthesis, structure, theoretical and experimental in vitro antioxidant/pharmacological properties of α-aryl, N-alkyl nitrones, as potential agents for the treatment of cerebral ischemia. *Bioorg. Med. Chem.* 2011, 19, 951-960; (b) Chioua, M.; Sucunza, D.; Soriano, E.; Hadjipavlou-Litina, D.; Alcázar, A.; Ayuso, I.; Oset-Gasque, M. J.; González, M. P.; Monjas, L.; Rodríguez-Franco, M. I.; Marco-Contelles, J.; Samadi, A. α-Aryl-N-alkyl Nitrones, as Potential Agents for Stroke Treatment: Synthesis, Theoretical Calculations, Antioxidant, Anti-inflammatory, Neuroprotective and Brain-Blood Barrier Permeability Properties, *J. Med. Chem.* 2012, 55, 153-168; (c) Arce, C.; Díaz-Castroverde, S.; Canales, M. J.; Marco-Contelles, J.; Samadi, A.; Oset-Gasque, M. J.; González, M. P. Drugs for stroke: Action of nitrone (Z)— N-(2-bromo-5-hydroxy-4-methoxybenzylidene)-2-methyl-propan-2-amine oxide on rat cortical neurons in culture subjected to oxygen-glucose-deprivation. *Eur. J. Med. Chem.* 2012, 55, 475-479], and based on the current prior art described above, hybrid molecules have been developed in a laboratory which combine and juxtapose a "steroid" motif and another "nitrone" motif, resulting in the new chemical entities referred to as "steroidal nitrones".

Although steroidal nitrones have been known for years [(a) Weintraub, P. M.; Tiernan, P. L. Steroidal nitrones, *J. Org. Chem.* 1974, 39, 1061-1065; (b) Joseph, S. P.; Dhar, D. N. Reaction of chlorosulfonyl isocyanate with nitrones: An efficient method for the synthesis of cyclic enamides and 2H-pyrroles. *Tetrahedron* 1988, 44, 5209-5214; (c) Hwu, J. R.; Khoudary, K. P.; Tsay, S.-C. Selectivity of the bulky proton-containing reagent N-methyl-N,O-bis(trimethylsilyl) hydroxylamine in the formation of nitrones, *J. Organometallic Chem.* 1990, 399, C13-C17; (d) Barton, D. H. R.; Day, M. J.; Hesse, R. H. A new rearrangement of ketonic nitrones: A convenient alternative to the Beckmann rearrangement. *J. Chem. Soc.; Perkin Trans.* 1975, 1764-1767; (e) Barton, D. H. R.; Choi, L. S. L.; Lister-James, J.; Hesse, R. H. Preparation and reactions of steroidal cross-conjugated 3-nitrones. *J. Chem. Soc.; Perkin Trans.* 1982, 2599-2606], the pharmacological activity and possible application thereof in defined therapies against given diseases surprisingly have barely been exploited and researched [(a) Blasig, L. E.; Mertsch, K.; Haseloff, R. F. Nitronyl nitroxides, a novel group of protective agents against oxidative stress in endothelial cells forming the blood-brain-barrier, *Neuropharmacology* 2002, 43, 1006-1014; (b) Robinson, A. J.; of Lucca, I.; Drummond, S.; Bosewell, G. A. Steroidal nitrone inhibitors of 5α-reductase, *Tetrahedron Lett.* 2003, 44, 4801-4804].

This patent therefore describes the use of neuroprotective, antioxidant steroidal nitrones of formula Ia-c and geometric isomers E and Z thereof, to which the blood-brain barrier is highly permeable, as potential agents and drugs for the treatment of a cerebral stroke or ischaemia, Alzheimer's and Parkinson's disease and amyotrophic lateral sclerosis, and where,

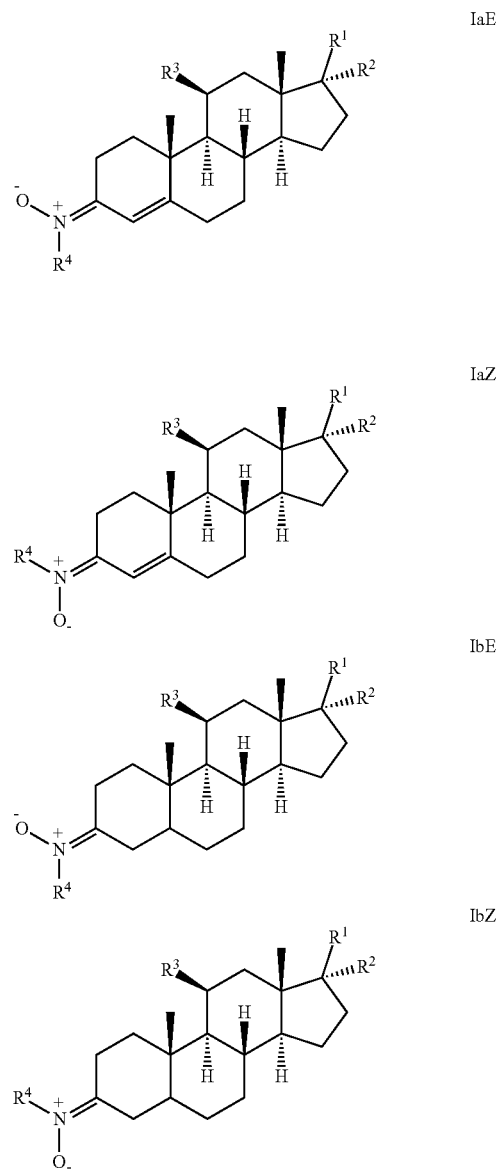

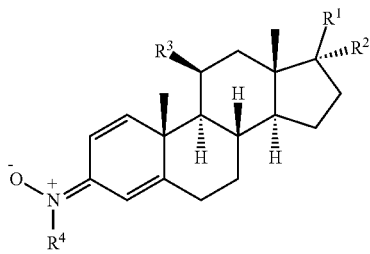

IcE

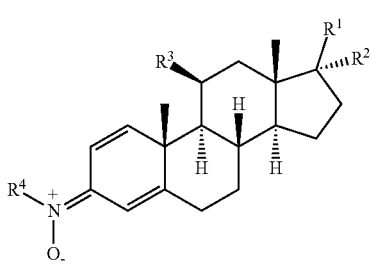

IcZ

R¹ independently represents a substituted or unsubstituted C1-C10 alkyl radical, α-hydroxyketone, α-methylketone, or hydroxyl groups, halogen, ether with a substituted or unsubstituted C1-C10 alkyl radical, primary, secondary amine with a substituted or unsubstituted C1-C10 alkyl radical; tertiary amine with two substituted or unsubstituted C1-C10 alkyl radicals;

R² represents a hydrogen atom, a substituted or unsubstituted C1-C10 alkyl radical, hydroxyl, halogen, ether with a substituted or unsubstituted C1-C10 alkyl radical, primary, secondary amine with a substituted or unsubstituted C1-C10 alkyl radical; tertiary amine with two substituted or unsubstituted C1-C10 alkyl radicals, or an acyloxy group (OCOX), where X can be a substituted or unsubstituted C1-C10 alkyl radical, phenyl, or an aromatic ring substituted with halogen, nitro, cyano, amino or ether groups with a substituted or unsubstituted C1-C10 alkyl radical, heterocyclic pyrrole, pyridine, indole, furan, or thiophenol ring;

R³ represents a hydrogen atom, or an acyloxy group (OCOX) where X can be a substituted or unsubstituted C1-C10 alkyl radical, phenyl, or an aromatic ring substituted with halogen, nitro, cyano, amino or ether groups with a substituted or unsubstituted C1-C10 alkyl radical, heterocyclic pyrrole, pyridine, indole, furan, or thiophenol ring; and R⁴ represents a methyl, t-butyl or benzyl group.

Conventional though non-limiting examples of this family of compounds are:

(E)-N-((8S,9S,10R,13R,14S,17R)-10,13-dimethyl-17-((R)-6-methylheptan-2-yl)-7,8,9,11,12,13,14,15,16,17-decahydro-1H-cyclopenta[a]phenanthren-3(2H,6H,10H)-ylidene)methanamine oxide (F2), and (Z)—N-((8S,9S,10R,13R,14S,17R)-10,13-dimethyl-17-((R)-6-methylheptan-2-yl)-7,8,9,11,12,13,14,15,16,17-decahydro-1H-cyclopenta[a]phenanthren-3(2H,6H,10H)-ylidene)methanamine oxide (F3), prepared from 4-cholesten-3-one or 5-cholesten-3-one by reaction with N-methylhydroxylamine, according to the following scheme.

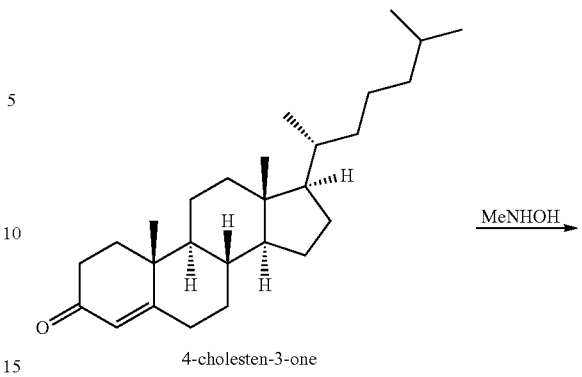

4-cholesten-3-one

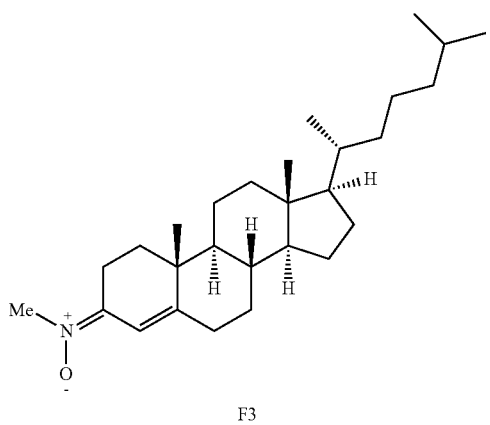

F3

+

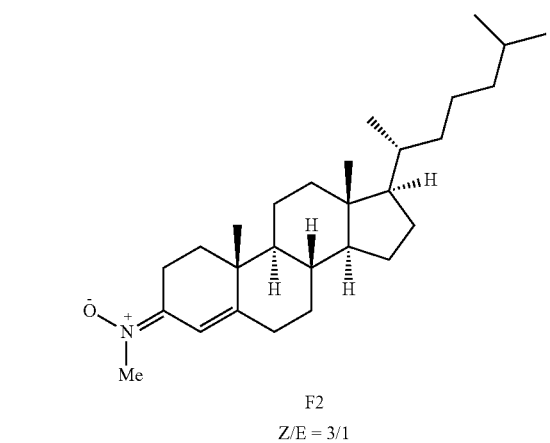

F2

Z/E = 3/1

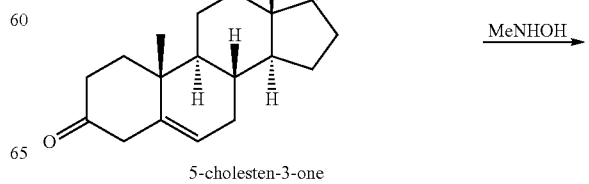

5-cholesten-3-one

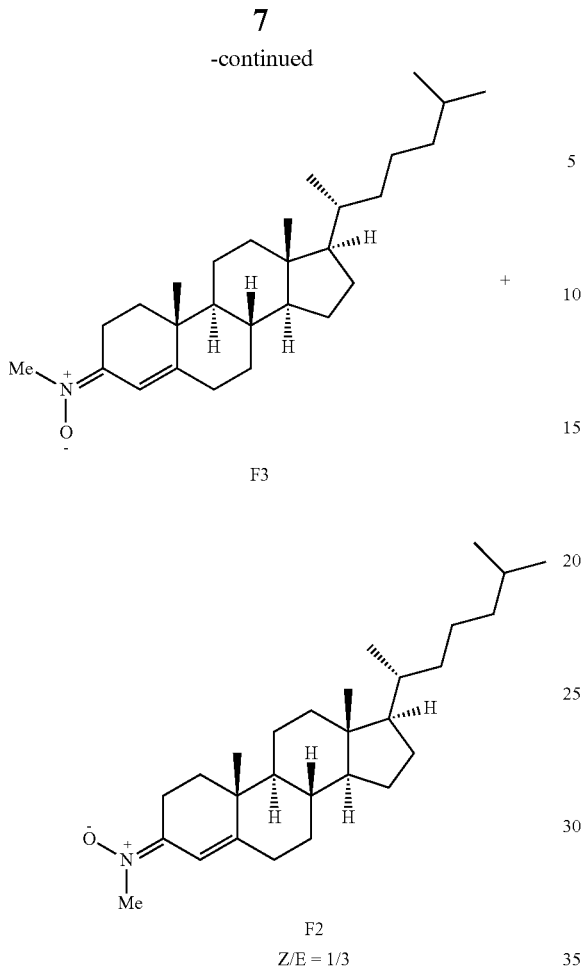

F3

F2

Z/E = 1/3

Additionally, any of the compounds mentioned as examples throughout the present invention can be used separately or in combination, particularly as adjuvant therapy administered simultaneously, alternatively or successively with respect to a first-line therapy suitable for the treatment of a neurological disease, such as cerebral ischaemia, Alzheimer's disease, Parkinson's disease and amyotrophic lateral sclerosis. In this sense, the steroidal nitrones of formula Ia-c administered simultaneously, alternatively or successively with respect to a thrombolytic agent, result in particularly suitable therapy for the treatment of cerebral ischaemia, particularly acute cerebral ischaemia.

Therefore, one aspect of the present invention relates to a composition comprising a steroidal nitrone derivative of formula Ia-c, and geometric isomers E and Z thereof in double bond $R^4N(O)=C(3)$, Ia Ib Ic where $R^1$ independently represents a substituted or unsubstituted C1-C10 alkyl radical, α-hydroxyketone, α-methylketone, or hydroxyl groups, halogen, ether with a substituted or unsubstituted C1-C10 alkyl radical, primary, secondary amine with a substituted or unsubstituted C1-C10 alkyl radical; tertiary amine with two substituted or unsubstituted C1-C10 alkyl radicals;

$R^2$ represents a hydrogen atom, a substituted or unsubstituted C1-C10 alkyl radical, hydroxyl, halogen, ether with a substituted or unsubstituted C1-C10 alkyl radical, primary, secondary amine with a substituted or unsubstituted C1-C10 alkyl radical; tertiary amine with two substituted or unsubstituted C1-C10 alkyl radicals, or an acyloxy group (OCOX), where X can be a substituted or unsubstituted C1-C10 alkyl radical, phenyl, or an aromatic ring substituted with halogen, nitro, cyano, amino or ether groups with a substituted or unsubstituted C1-C10 alkyl radical, heterocyclic pyrrole, pyridine, indole, furan, or thiophenol ring; and $R^3$ represents a hydrogen atom, or an acyloxy group (OCOX) where X can be a substituted or unsubstituted C1-C10 alkyl radical, phenyl, or an aromatic ring substituted with halogen, nitro, cyano, amino or ether groups with a substituted or unsubstituted C1-C10 alkyl radical, heterocyclic pyrrole, pyridine, indole, furan, or thiophenol ring; and $R^4$ represents a methyl, t-butyl or benzyl group;

for use as adjuvant therapy administered simultaneously, alternatively or successively with respect to a first-line therapy suitable for the treatment of a neurological disease, such as cerebral ischaemia, Alzheimer's disease, Parkinson's disease and amyotrophic lateral sclerosis. The steroidal nitrone derivative is preferably selected from the list consisting of cholesteronitrone F2 and F3.

Alternatively, this aspect of the invention relates to the use of a composition comprising the steroidal nitrone derivative defined above for the preparation of a medicament for use as adjuvant therapy administered simultaneously, alternatively or successively with respect to a first-line therapy suitable for the treatment of a neurological disease, such as cerebral ischaemia, Alzheimer's disease, Parkinson's disease and amyotrophic lateral sclerosis. The steroidal nitrone derivative is preferably selected from the list consisting of cholesteronitrone F2 and F3.

Another aspect of the present invention relates to a composition comprising the steroidal nitrone derivative defined above, preferably the steroidal nitrone derivative selected from the list consisting of cholesteronitrone F2 and F3, for the preparation of a medicament for use as adjuvant therapy administered simultaneously, alternatively or successively with respect to a first-line therapy suitable for the treatment of the cerebral ischaemia, where said primary or first-line treatment comprises the use of a thrombolytic agent, preferably the use of tissue plasminogen activator (rt-PA).

Additionally, the present invention relates to a method for identifying and evaluating, in a rapid and optionally robotic manner, compounds having high neuroprotective power and involving a possible effective treatment for neurological diseases, such as cerebral ischaemia, Alzheimer's disease, Parkinson's disease and amyotrophic lateral sclerosis.

Steroidal nitrone derivatives of formula Ia-c and geometric isomers E and Z thereof in double bond $R^4N(O)=C(3)$ are used to carry out said drug screening,

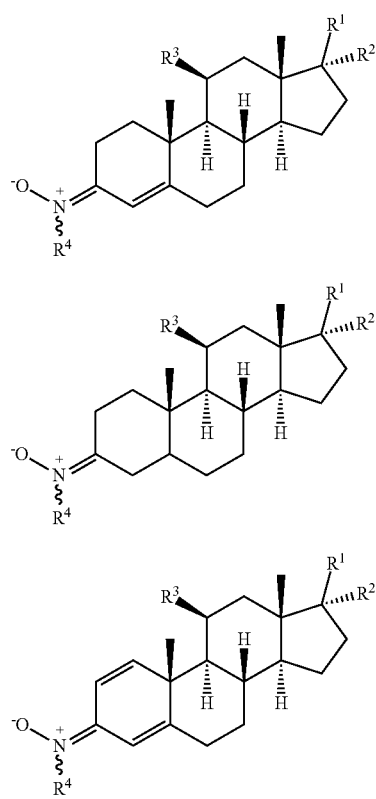

where $R^1$ independently represents a substituted or unsubstituted C1-C10 alkyl radical, α-hydroxyketone, α-methylketone, or hydroxyl groups, halogen, ether with a substituted or unsubstituted C1-C10 alkyl radical, primary, secondary amine with a substituted or unsubstituted C1-C10 alkyl radical; tertiary amine with two substituted or unsubstituted C1-C10 alkyl radicals;

$R^2$ represents a hydrogen atom, a substituted or unsubstituted C1-C10 alkyl radical, hydroxyl, halogen, ether with a substituted or unsubstituted C1-C10 alkyl radical, primary, secondary amine with a substituted or unsubstituted C1-C10 alkyl radical; tertiary amine with two substituted or unsubstituted C1-C10 alkyl radicals, or an acyloxy group (OCOX), where X can be a substituted or unsubstituted C1-C10 alkyl radical, phenyl, or an aromatic ring substituted with halogen, nitro, cyano, amino or ether groups with a substituted or unsubstituted C1-C10 alkyl radical, heterocyclic pyrrole, pyridine, indole, furan, or thiophenol ring; and $R^3$ represents a hydrogen atom, or an acyloxy group (OCOX), where X can be a substituted or unsubstituted C1-C10 alkyl radical, phenyl, or an aromatic ring substituted with halogen, nitro, cyano, amino or ether groups with a substituted or unsubstituted C1-C10 alkyl radical, heterocyclic pyrrole, pyridine, indole, furan, or thiophenol ring; and $R^4$ represents a methyl, t-butyl or benzyl group.

To verify the neuroprotective activity of said steroidal nitrones of formula Ia-c and to enable selecting those compounds with the highest activity, their neuroprotective power is determined using any in vitro or in vivo model or assay suited to that end. Said models or assays are known for the person skilled in the art; nevertheless, and merely by way of example, a possible assay for determining the neuroprotective activity of steroidal nitrones of formula Ia-c and their possible usefulness in the treatment of neurological diseases, would be in primary neuronal cultures, cultured from 6 to 8 days, taken from the cerebral cortex of rats, where cell viability is determined (Quevedo, C, Salinas, M, Alcázar, A. Initiation factor 2B activity is regulated by protein phosphatase 1, which is activated by the mitogen-activated protein kinase-dependent pathway in insulin-like growth factor 1-stimulated neuronal cells. *J. Biol. Chem.* 2003, 278, 16579-16586), and subjected to oxygen-glucose deprivation (OGD) (Chioua M, Sucunza D, Soriano E, Hadjipavlou-Litina D, Alcázar A, Ayuso I, Oset-Gasque M J, González M P, Monjas L, Rodríguez-Franco M I, Marco-Contelles J, Samadi A. α-aryl-N-alkyl nitrones, as potential agents for stroke treatment: synthesis, theoretical calculations, antioxidant, anti-inflammatory, neuroprotective, and brain-blood barrier permeability properties. *J Med Chem.* 2012, 55, 153-168), according to the following protocol:

Cell viability is measured using 3-(4,5-dimethylthiazol-2-yl)-2,5-diphenyl tetrazolium bromide (MTT). Therefore, exposure of the neuronal cultures to OGD for 4 h (OGD 4 h) induces a significant decrease in cell viability of 67.3% (p<0.0001 versus 100% control, one-sample test), which is partially reverted 24 hours after reperfusion (R24h, 76.1%; p<0.0022 versus OGD 4 h, Student's t-test), but it does not reach the control value at 24 h (p<0.0001 versus 100% control, one-sample t-test). In this sense, to evaluate the neuroprotective power of the steroidal nitrones of formula Ia-c, they are added to the primary culture at the beginning of the reperfusion period, using citicoline, a well-known neuroprotective agent, as a reference compound. Those steroidal nitrones of formula Ia-c having higher neuroprotective power with respect to citicoline are selected.

Additionally and also by way of example, a second model which allows selecting those steroidal nitrones of formula Ia-c having higher neuroprotective power would be by inducing global ischaemia in adult rats according to the conventional four-vessel occlusion method [(a) Martín de la Vega C, Burda J, Nemethova M, Quevedo C, Alcázar A, Martín M E, Salinas M. Possible mechanisms involved in the down-regulation of translation during transient global ischaemia in the rat brain. Biochem J 2001, 357, 819-826; (b) García-Bonilla L, Cid C, Alcázar A, Burda J, Ayuso I, Salinas M. Regulation proteins of eukaryotic initiation factor 2-alpha subunit (eIF2a) phosphatase, under ischemic reperfusion and tolerance. J Neurochem 2007, 103, 1368-1380; (c) Ayuso M I, Hernández-Jiménez M, Martín M E, Salinas M, Alcázar A. New hierarchical phosphorylation pathway of the translational repressor eIF4E-binding protein 1 (4E-BP1) in ischaemia-reperfusion stress. J Biol Chem 2010, 285, 34355-34363].

Therefore, the two vertebral arteries are completely cauterized, and after 24 h ischaemia is induced by carotid occlusion by means of small clamps for 15 min; the clamps are then removed and reperfusion is performed. After 5 d (R5d), the animals are sacrificed. To determine the neuroprotective power of steroidal nitrones of formula Ia-c, the animals are treated with steroidal nitrones of formula Ia-c from the beginning of the reperfusion period. The protective effect of steroidal nitrones with respect to stress-induced IR due to neuronal death can be observed with Fluoro-Jade B (Burda J, Matiasov M, Gottlieb M, Danielisov V, Nemethov M, García L, et al. Evidence for a role of second pathophysiological stress in prevention of delayed neuronal death in the hippocampal CA1 region. Neurochem Res 2005, 30, 1397-1405), and it can be viewed under fluorescence microscopy. These experiments allow showing whether or not treatment with different steroidal nitrones reduces neuronal death, and, therefore, selecting those having higher neuroprotective power.

Therefore, an additional aspect of the invention relates to a method for identifying and evaluating, in a rapid and optionally robotic manner, compounds having high neuroprotective power and involving a possible effective treatment for neurological diseases, such as cerebral ischaemia, Alzheimer's and Parkinson's disease and amyotrophic lateral sclerosis, comprising the following steps:

selecting one or more steroidal nitrone derivatives of formula Ia-c, and geometric isomers E and Z thereof in double bond $R^4N(O)=C(3)$;

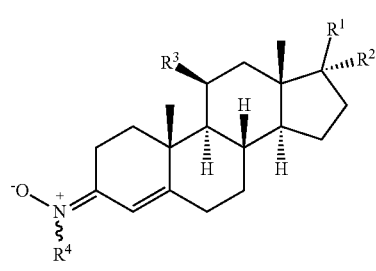

Ia

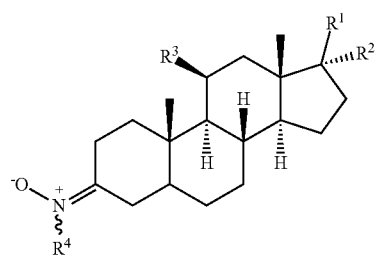

Ib

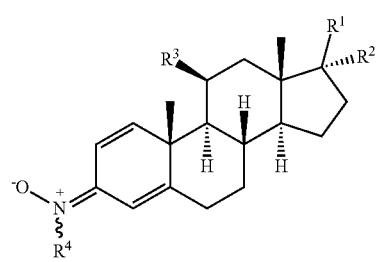

Ic where $R^1$ independently represents a substituted or unsubstituted C1-C10 alkyl radical, α-hydroxyketone, α-methylketone, or hydroxyl groups, halogen, ether with a substituted or unsubstituted C1-C10 alkyl radical, primary, secondary amine with a substituted or unsubstituted C1-C10 alkyl radical; tertiary amine with two substituted or unsubstituted C1-C10 alkyl radicals;

$R^2$ represents a hydrogen atom, a substituted or unsubstituted C1-C10 alkyl radical, hydroxyl, halogen, ether with a substituted or unsubstituted C1-C10 alkyl radical, primary, secondary amine with a substituted or unsubstituted C1-C10 alkyl radical; tertiary amine with two substituted or unsubstituted C1-C10 alkyl radicals, or an acyloxy group (OCOX), where X can be a substituted or unsubstituted C1-C10 alkyl radical, phenyl, or an aromatic ring substituted with halogen, nitro, cyano, amino or ether groups with a substituted or unsubstituted C1-C10 alkyl radical, heterocyclic pyrrole, pyridine, indole, furan, or thiophenol ring; and $R^3$ represents a hydrogen atom, or an acyloxy group (OCOX), where X can be a substituted or unsubstituted C1-C10 alkyl radical, phenyl, or an aromatic ring substituted with halogen, nitro, cyano, amino or ether groups with a substituted or unsubstituted C1-C10 alkyl radical, heterocyclic pyrrole, pyridine, indole, furan, or thiophenol ring; and $R^4$ represents a methyl, t-butyl or benzyl group;

determining the neuroprotective activity of said steroidal nitrones of formula Ia-c through a model or assay allowing said determination; preferably using any of the methods or assays illustrated throughout the present invention;

comparing said neuroprotective activity with a reference compound or with a reference value; and selecting those compounds with the highest activity.

Additionally, another aspect of the invention relates to a method for obtaining compounds having high neuroprotective power and involving a possible effective treatment for neurological diseases, such as cerebral ischaemia, Alzheimer's and Parkinson's disease and amyotrophic lateral sclerosis, comprising the following steps:

selecting one or more steroidal nitrone derivatives of formula Ia-c, and geometric isomers E and Z thereof in double bond $R^4N(O)=C(3)$;

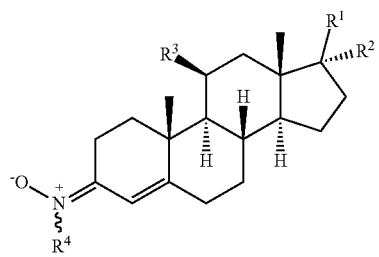

Ia

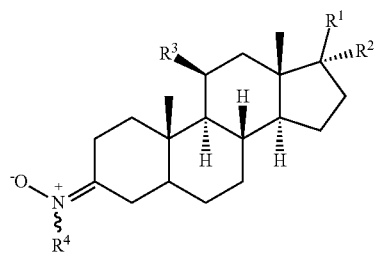

Ib

-continued

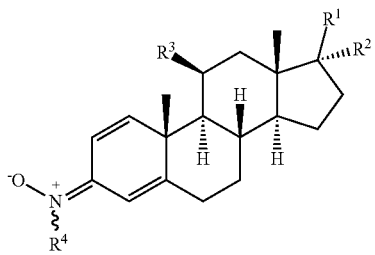

Ic where R¹ independently represents a substituted or unsubstituted C1-C10 alkyl radical, α-hydroxyketone, α-methylketone, or hydroxyl groups, halogen, ether with a substituted or unsubstituted C1-C10 alkyl radical, primary, secondary amine with a substituted or unsubstituted C1-C10 alkyl radical; tertiary amine with two substituted or unsubstituted C1-C10 alkyl radicals;

R² represents a hydrogen atom, a substituted or unsubstituted C1-C10 alkyl radical, hydroxyl, halogen, ether with a substituted or unsubstituted C1-C10 alkyl radical, primary, secondary amine with a substituted or unsubstituted C1-C10 alkyl radical; tertiary amine with two substituted or unsubstituted C1-C10 alkyl radicals, or an acyloxy group (OCOX), where X can be a substituted or unsubstituted C1-C10 alkyl radical, phenyl, or an aromatic ring substituted with halogen, nitro, cyano, amino or ether groups with a substituted or unsubstituted C1-C10 alkyl radical, heterocyclic pyrrole, pyridine, indole, furan, or thiophenol ring; and R³ represents a hydrogen atom, or an acyloxy group (OCOX) where X can be a substituted or unsubstituted C1-C10 alkyl radical, phenyl, or an aromatic ring substituted with halogen, nitro, cyano, amino or ether groups with a substituted or unsubstituted C1-C10 alkyl radical, heterocyclic pyrrole, pyridine, indole, furan, or thiophenol ring; and R⁴ represents a methyl, t-butyl or benzyl group;

determining the neuroprotective activity of said steroidal nitrones of formula Ia-c through a model or assay allowing said determination; preferably using any of the methods or assays illustrated throughout the present invention;

comparing said neuroprotective activity with a reference compound or with a reference value; and selecting those compounds with the highest activity;

isolating said selected compounds preferably in a substantially pure form.

The following examples serve to illustrate the present invention but in no case are limiting thereof.

EXAMPLES

The melting points were determined in Koffler equipment and are not corrected. The ¹H NMR and ¹³C NMR spectra were obtained at room temperature, at 300, 400 or 500 MHz, and at 75, 100 or 125 MHz, respectively, using CDCl₃ or DMSO-d₆ as solvents and the peaks of these deuterated solvents as internal references (CDCl₃: 7.27 (D), 77.2 (C) ppm; D₂O: 4.60 ppm and DMSO-d₆: 2.49 (D), 40 (C)). The chemical shift assignment of the compounds is determined according to the data obtained in standard NMR experiments ((¹H, ¹³C-DEPT, ¹H, ¹H-COSY, gHSQC, gHMBC). The mass spectrometry analyses were carried out in GC/MS equipment with an API-ES type ionization source. The microanalyses were performed in the CQO (CSIC, Madrid).

Thin-layer chromatography was carried out in F254 silica gel plates, and ultraviolet light or the ninhydrin developers, anisaldehyde and phosphomolybdic acid-H₂SO₄ were used for viewing. All the reactions were performed using dry solvents. The chromatography columns were 0.06 mm silica gel columns (230 mesh).

Example 1. General Method for Nitrone Synthesis

A solution of ketone (1 mmol), Na₂SO₄ (3 mmol), and triethylamine (2 mmol) was suspended in EtOH and treated with the hydroxylamine hydrochloride (1.5 mmol). The mixture was stirred for 30 seconds and irradiated in a microwave oven (250 W) at 90° C. When the reaction was determined to have concluded (TLC analysis), the solvent was removed in vacuum, diluted with water, extracted with AcOEt, dried with Na₂SO₄, filtered and evaporated. The residue was purified by column chromatography.

Method A. Following the general method, the reaction of 4-cholesten-3-one (385 mg, 1 mmol), Na₂SO₄ (426 mg, 3 mmol), Et₃N (0.30 mL, 2 mmol), and N-methylhydroxylamine hydrochloride (126 mg, 1.5 mmol) in ethanol (10 mL), in 3 h of reaction, and after column chromatography (CH₂Cl₂/MeOH, from 1% to 2%), yielded a separable mixture of ChN F2 and ChN F3 (396 mg, 96%, at a 1:3 ratio).

Method B. Following the general method, the reaction of 5-cholesten-3-one (385 mg, 1 mmol), Na₂SO₄ (426 mg, 3 mmol), Et₃N (0.30 mL, 2 mmol), and N-methylhydroxylamine hydrochloride (126 mg, 1.5 mmol) in ethanol (10 mL), in 2 h of reaction and after column chromatography (CH₂Cl₂/MeOH, from 1% a 2%), yielded a separable mixture of ChN F2 and ChN F3 (407 mg, 98%, at a 3:1 ratio).

ChN (F2): White solid; Rf (0.21, CH$_2$Cl$_2$/MeOH, 5%); mp 139-141° C.; IR (KBr) v 2939, 2868, 2849, 1466, 1215 cm$^{-1}$; $^1$H NMR (400 MHz, CDCl$_3$) δ5.97 (d, J=2.0 Hz, 1H, $^4$CH), 3.72 (s, 3H, NCH$_3$), 3.23 (d, J=18.4 Hz, 1H, $^2$CH), 2.34 (m, 2H, $^6$CH$_2$), 2.21 (m, 1H, $^2$CH), 1.99 (m, 2H, CH$_2$), 1.80 (m, 2H, CH$_2$), 1.60 (s, 3H, CH$_3$), 1.36 (m, 10H, $^5$CH$_2$), 1.12 (m, 6H, 6CH$_2$), 1.04 (s, 3H, $^{19}$CH$_3$), 0.99 (m, 2H, CH$_2$), 0.91 (d, J=6.4 Hz, 3H, $^{21}$CH$_3$), 0.88 (d, J=1.3 Hz, 3H, $^{26}$CH$_3$), 0.86 (m, 3H, $^{27}$CH$_3$), 0.70 (s, 3H, $^{18}$CH$_3$); $^{13}$C NMR (101 MHz, CDCl$_3$) δ156.8 ($^3$C), 146.4 ($^5$C), 112.9 ($^4$CH), 56.1 ($^{17}$CH), 55.9 ($^{14}$CH), 53.5 ($^9$CH), 46.0 ($^{13}$C), 42.3 (NCH$_3$), 39.6 (C), 39.4 (C), 37.9 ($^{10}$C), 36.1 (C), 35.77 (C), 35.73 (C), 34.4 (C), 33.4 (C), 32.2 ($^{25}$CH$_2$), 28.1 ($^{16}$CH$_2$), 27.9 ($^2$CH$_2$), 24.2 ($^{15}$CH$_2$), 23.8 ($^{24}$CH$_2$), 22.7 ($^{26}$CH$_3$), 22.5 ($^{27}$CH$_3$), 21.4 (CH$_2$), 21.3 ($^{11}$CH), 18.6 ($^{19}$CH$_3$), 17.8 ($^{21}$CH$_3$), 11.9 ($^{18}$CH$_3$). MS (EI) m/z: 413 (M, 37%)+, 398 (M−CH$_3$, 27%), 397 (M-O, 70), 137 (C$_8$H$_{11}$NO, 100%); MS (ESI) m/z: 414.2 (M+H)$^+$, 436.2 (M+Na)$^+$, 827.8 (2M)+, 849.7 (2M+Na)$^+$, Anal. calcd. for C$_{28}$H$_{47}$NO: C, 81.29; H, 11.45; N, 3.39. Found: C, 80.98; H, 12.19; N, 3.44.

ChN (F3): White solid: Rf (0.20, CH$_2$Cl$_2$/MeOH, 5%); mp 153-5° C. IR (KBr) v 2936, 2868, 1629, 1214 cm$^{-1}$; $^1$H NMR (400 MHz, CDCl$_3$) δ6.78 (s, 1H, $^4$CH), 3.66 (s, 3H, NCH$_3$), 2.44 (m, 4H, 2CH$_2$), 1.88 (m, 4H, 2CH$_2$), 1.37 (m, 14H, 7CH$_2$), 1.04 (s, 3H, $^{19}$CH$_3$), 0.98 (m, 2H, CH$_2$), 0.91 (d, J=6.4 Hz, 3H, $^{21}$CH$_3$), 0.88 (d, J=1.4 Hz, 3H, $^{26}$CH$_3$), 0.85 (d, J=1.4 Hz, 3H, $^{27}$CH$_3$), 0.70 (s, 3H, $^{18}$CH$_3$); $^{13}$C NMR (101 MHz, CDCl$_3$) δ123.7 ($^3$C), 120.3 ($^5$C), 113.7 ($^4$CH), 56.0 ($^{17}$CH), 55.9 ($^{14}$CH), 53.5 ($^9$CH), 46.4 ($^{13}$C), 42.3 (NCH$_3$), 39.6 (C), 39.4 (C), 37.9 ($^{10}$C), 36.0 (C), 35.72 (C), 35.71 (C), 35.4 (C), 32.9 (C), 32.2 (C), 28.1 (C), 27.9 (C), 24.1 ($^{16}$CH$_2$), 23.7 ($^{15}$CH$_2$), 23.6 ($^{24}$CH$_2$), 22.7 ($^{26}$CH$_3$), 22.5 ($^{27}$CH$_3$), 21.3 ($^{11}$CH$_2$), 18.6 ($^{19}$CH$_3$), 17.8 ($^{21}$CH$_3$), 11.9 ($^{18}$CH$_3$). MS (EI) m/z: 413 (M, 37%)$^+$, 398

(M-CH$_3$, 27%), 397 (M-O, 70), 137 (C$_8$H$_{11}$NO, 100%); MS (ESI) m/z: 414.2 (M+H)$^+$, 827.8 (2M)+, 849.7 (2M+Na)$^+$. Anal. calcd. for C$_{28}$H$_{47}$NO: C, 81.29; H, 11.45; N, 3.39. Found: C, 81.03; H, 11.33; N, 3.30, Pharmacological Evaluation of the Neuroprotection Against Ischaemia The neuroprotective power of cholesteronitrones F2 and F3 has been determined in primary neuronal cultures, cultured from 6 to 8 days, taken from the cerebral cortex of rats (Quevedo, C, Salinas, M, Alcázar, A. Initiation factor 2B activity is regulated by protein phosphatase 1, which is activated by the mitogen-activated protein kinase-dependent pathway in insulin-like growth factor 1-stimulated neuronal cells. *J. Biol. Chem.* 2003, 278, 16579-16586), and subjected to oxygen-glucose deprivation (OGD) (Chioua M, Sucunza D, Soriano E, Hadjipavlou-Litina D, Alcázar A, Ayuso I, Oset-Gasque M J, González M P, Monjas L, Rodríguez-Franco M I, Marco-Contelles J, Samadi A. α-aryl-N-alkyl nitrones, as potential agents for stroke treatment: synthesis, theoretical calculations, antioxidant, antiinflammatory, neuroprotective, and brain-blood barrier permeability properties. *J Med Chem.* 2012, 55, 153-168), according to the following protocol:

Cell viability was measured using 3-(4,5-dimethylthiazol-2-yl)-2,5-diphenyl tetrazolium bromide (MTT). Therefore, exposure of the neuronal cultures to OGD for 4 h (OGD 4 h) induced a significant decrease in cell viability of 67.3% ($p<0.0001$ versus 100% control, one-sample test), which was partially reverted 24 hours after reperfusion (R24h, 76.1%; $p<0.0022$ versus OGD 4 h, Student's t-test), but it does not reach the control value at 24 h ($p<0.0001$ versus 100% control, one-sample t-test) (FIG. 1).

Cholesteronitrones F2 and F3, in a range of concentrations from 0.1 to 100 µM, and from 0.5 to 10 µM, respectively, were added at the beginning of the reperfusion period to evaluate their neuroprotective power, using citicoline, a well-known neuroprotective agent, as a reference compound (Adibhatla, R M, Hatcher, J F, Dempsey, R J. Citicoline: neuroprotective mechanisms in cerebral ischemia. *J. Neurochem.* 2002, 80, 12-23). Citicoline was tested at variable concentrations, between 1 µM and 1 mM, a neuroprotective effect being found at 10 and 100 µM (87.4 and 88.1%, respectively), the effect of 100 µM being significant compared with the value obtained at R24h (analysis of variance (ANOVA), $p<0.0021$; and $p<0.01$, post-Dunnett test].

The addition of cholesteronitrone F2 at 1 or 5 µM, but not cholesteronitrone F3, significantly increased neuronal viability during reperfusion, and at the concentration of 5 µM, the control value was almost reached (89.1 and 95.5%, for cholesteronitrone F2 at 1 or 5 µM, respectively; ANOVA, $p<0.0001$; and $p<0.01$, post-Dunnett test compared with R24h) (FIG. 1).

The neuroprotection induced by cholesteronitrone F2 was compared with the neuroprotection induced by citicoline at 5 µM, which resulted in a significantly higher neuroprotection than that observed for citicoline (Table 1).

TABLE 1

Neuroprotective effect of cholesteronitrones F2 and F3 in neuronal cultures in OGD conditions.

| Cholesteronitrone | Concentration (µM) | Neuroprotection (%) |
|---|---|---|
| F2 | 0.1 | 9.6 ± 0.5 |
|  | 0.5 | 49.3 ± 3.6 |
|  | 1.0 | 54.3 ± 1.3 * |
|  | 5.0 | 80.7 ± 2.7 ** |
|  | 10 | 47.2 ± 1.4 |
|  | 50 | <0 |
|  | 100 | <0 |
| F3 | 0.5 | <0 |
|  | 1.0 | 18.8 ± 1.1 |
|  | 5.0 | 21.7 ± 1.2 |
|  | 10 | 0.8 ± 0.07 |
| citicoline | 100 | 50.2 ± 1.26 |

In contrast, the cholesteronitrone F3 did not show significant neuroprotective capacity.

To evaluate the neuroprotective power of cholesteronitrones F2 and F3 against ischaemic damage in cultured neurons and simulate long-term reperfusion conditions, the cultures were exposed to OGD for 4 h, and the cells were then subjected to reperfusion for 5 d (R5d).

Cholesteronitrones F2 and F3 (at concentrations of 1.0 and 5.0 µM) were added at the beginning of the reperfusion period and after 48 h of reperfusion, to thus evaluate their long-term neuroprotective power, again using the reference molecule citicoline, according to the protocol of the MTT (see above).

Figure 2:
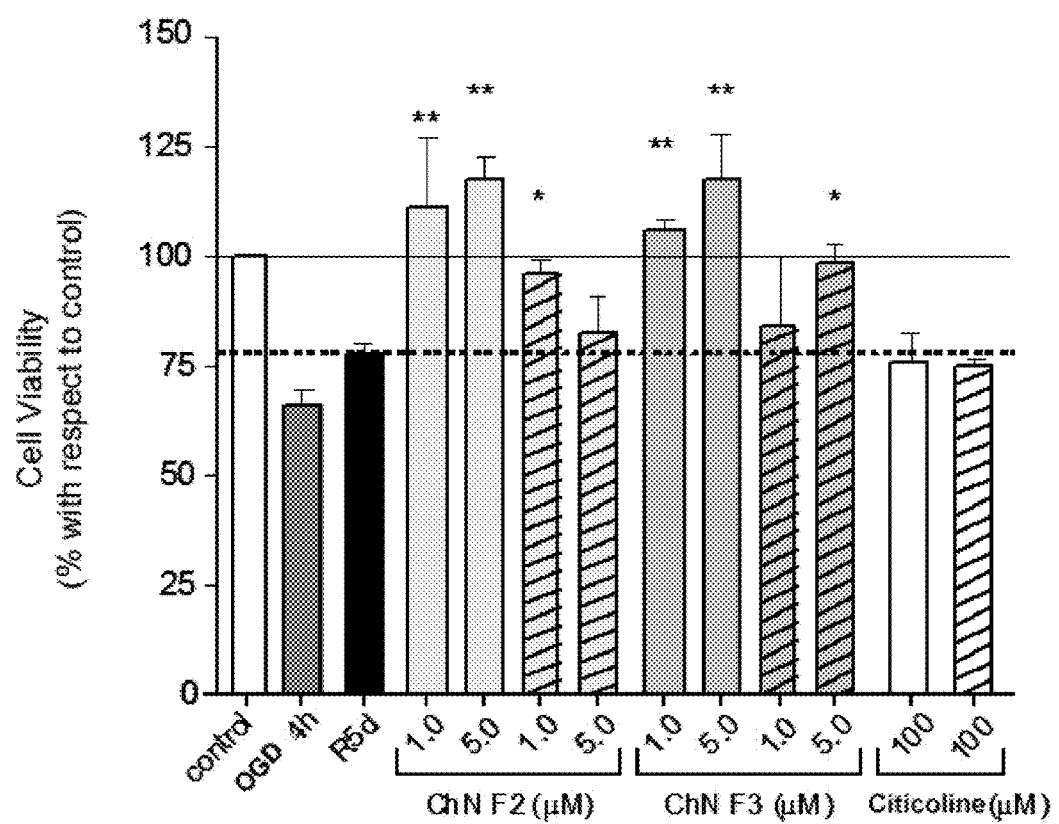
FIG. 2 shows how R5d experiment induced a more than noticeable decrease in cell viability (77.7%; p<0.0001 versus 100% of the control, one-sample t-test).

The R5d experiment induced a more than noticeable decrease in cell viability (77.7%; $p<0.0001$ versus 100% of the control, one-sample t-test) (FIG. 2). Citicoline, tested at a concentration of 100 µM, did not produce any neuroprotection in the R5d experiment both when it was added at the beginning of reperfusion (solid bar) or after 48 h of reperfusion (striped bar) (76.0 and 74.6%, respectively; ANOVA, p=0.786).

In contrast, the addition of cholesteronitrone F2 (or F3) at 1 and 5 µM, did produce a considerable increase in neuronal viability, exceeding the control value observed at 5 d (110.6 and 118.2%, at 1 and 5 µM for cholesteronitrone F2, respectively; 105.6 and 118.6%, at 1 and 5 µM for cholesteronitrone F3, respectively; ANOVA, $p<0.0001$; and $p<0.01$, Dunnett test) (FIG. 2, solid bars).

Furthermore, cholesteronitrone F2 (1 µM), or cholesteronitrone F3 (5 µM), added after 48 h of reperfusion (striped bars), significantly increased neuronal viability in the R5d experiment (95.7 and 97.8%, at 1 and 5 µM for cholesteronitrones F2 and F3, respectively; ANOVA, $p<0.0001$; and $p<0.05$, according to the Dunnett test compared with R5d) (FIG. 2, striped bars).

In summary, neuroprotection by cholesteronitrone after ischaemia has long-term effectiveness, and it was maintained even after 48 h of treatment, when citicoline no longer showed any effect.

Global ischaemia was induced in adult rats according to the conventional four-vessel occlusion method [(a) Martín de la Vega C, Burda J, Nemethova M, Quevedo C, Alcázar A, Martín M E, Salinas M. Possible mechanisms involved in the down-regulation of translation during transient global ischaemia in the rat brain. *Biochem J* 2001, 357, 819-826; (b) García-Bonilla L, Cid C, Alcázar A, Burda J, Ayuso I, Salinas M. Regulation proteins of eukaryotic initiation factor 2-alpha subunit (eIF2a) phosphatase, under ischemic reperfusion and tolerance. *J Neurochem* 2007, 103, 1368-1380; (c) Ayuso M I, Hernández-Jiménez M, Martín M E, Salinas M, Alcázar A. New hierarchical phosphorylation pathway of the translational repressor eIF4E-binding protein 1 (4E-BP1) in ischemia-reperfusion stress. *J Biol Chem* 2010, 285, 34355-34363].

Therefore, the two vertebral arteries were completely cauterized, and after 24 h ischaemia is induced by carotid occlusion by means of small clamps for 15 min; the clamps were then removed and reperfusion was performed. After 5 d (R5d), the animals were sacrificed. The animals were treated with cholesteronitrone F2, diluted in 10% ethanol in saline solution as a carrier, administered intraperitoneally from the beginning of the reperfusion period. Ten animals were tested; one of the five animals treated with carrier died 2 d after reperfusion. All the protocols used in the experiments with animals were performed according to the guidelines approved by the Ethics Committee of Hospital Ramón y Cajal (Madrid). In the model of four-vessel occlusion cerebral ischaemia in rats, after a brief period of ischaemia delayed neurodegeneration is produced in the CA1 region of the hippocampus [(a) Kirino T. Delayed neuronal death. *Neuropathology* 2000, 20, S95-S97; (b) Pulsinelli W A, Brierley J B, Plum F. Temporal profile of neuronal damage in a model of transient forebrain ischaemia. *Ann Neurol* 1982, 11, 491-498; (c) Burda J, Matiasov M, Gottlieb M, Danielisov V, Nemethov M, García L et al. Evidence for a role of second pathophysiological stress in prevention of delayed neuronal death in the hippocampal CA1 region. *Neurochem Res* 2005, 30, 1397-1405)]. In this model experimental, reperfusion from 3 to 7 d after ischaemia induces significant neuronal death in CA1 (Ayuso M I, Martínez-Alonso E, Cid C, de Leciñana M A, Alcázar A. The translational repressor eIF4E-binding protein 2 (4E-BP2) correlates with selective delayed neuronal death after ischemia. *J Cereb Blood Flow Metab.* At press, doi: 10.1038/jcbfm.2013.60). Selective neurodegeneration of the neurons in the CA1 area was evident compared with what was observed in the cerebral cortex.

Figure 3:
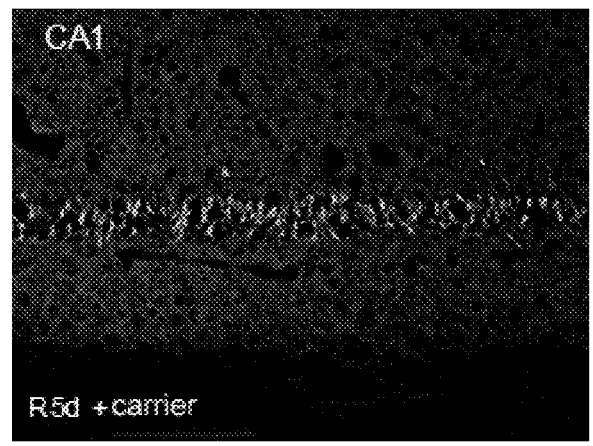
FIG. 3 shows how the animals treated with cholesteronitrone F2 showed a significant decrease in the apoptotic death in the CA1 region (CA1) in the experiment after 5 d (R5d) (70.4±2.4 compared with 55.1±3.4 cells per field, for animals treated with saline solution and cholesteronitrone F2, respectively; ANOVA, p<0.0001; and p<0.01, post-Newman-Keuls test).
Figure 3:
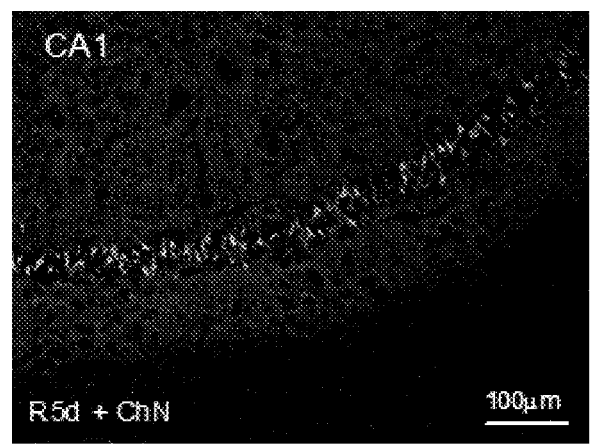
Figure 3:
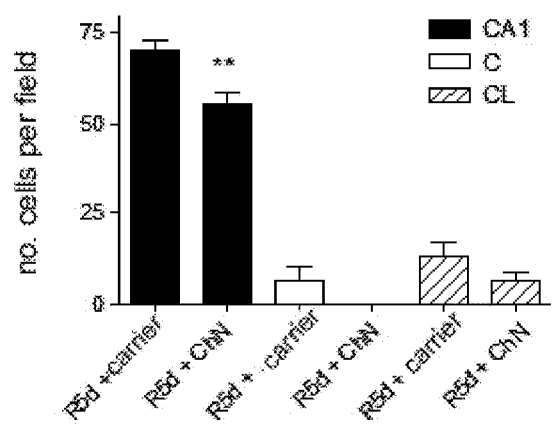

The animals were treated with cholesteronitrone F2 at a dose of 0.1 mg/kg from the very beginning of the reperfusion period, neuronal death being induced in 5 d (R5d). The protective effect of cholesteronitrone F2 against stress-induced IR due to neuronal death was observed with Fluoro-Jade B (Burda J, Matiasov M, Gottlieb M, Danielisov V, Nemethov M, García L et al. Evidence for a role of second pathophysiological stress in prevention of delayed neuronal death in the hippocampal CA1 region. *Neurochem Res* 2005, 30, 1397-1405), and it could be viewed under fluorescence microscopy. These experiments showed that treatment with cholesteronitrone significantly reduced neuronal death in the CA1 region of the hippocampus. The results showed that the animals treated with cholesteronitrone showed a significant decrease in apoptotic death in the CA1 region (CA1) in the 5 d experiment (R5d) (70.4±2.4 compared with 55.1±3.4 of cells per field, for animals treated with saline solution and cholesteronitrone F2, respectively; ANOVA, $p<0.0001$; and $p<0.01$, post-Newman-Keuls test) (FIG. 3, CA1). Neuronal death induced by ischaemia was also observed in the cerebral cortex (C) and lateral cortex (LC), although the effect was much more limited than in the CA1 region. Furthermore, the reduction in neuronal ischaemic damage due to cholesteronitrone F2 could be observed in the cerebral cortex (6.7±3.5 compared with 0±0.1 cells per field, for animals treated with carrier and cholesteronitrone, respectively; $p<0.05$, Student's t-test) and lateral cortex (13.4±3.6 compared with 6.3±2.2, for animals treated with carrier and cholesteronitrone, respectively) (FIG. 3).

Figure 4:
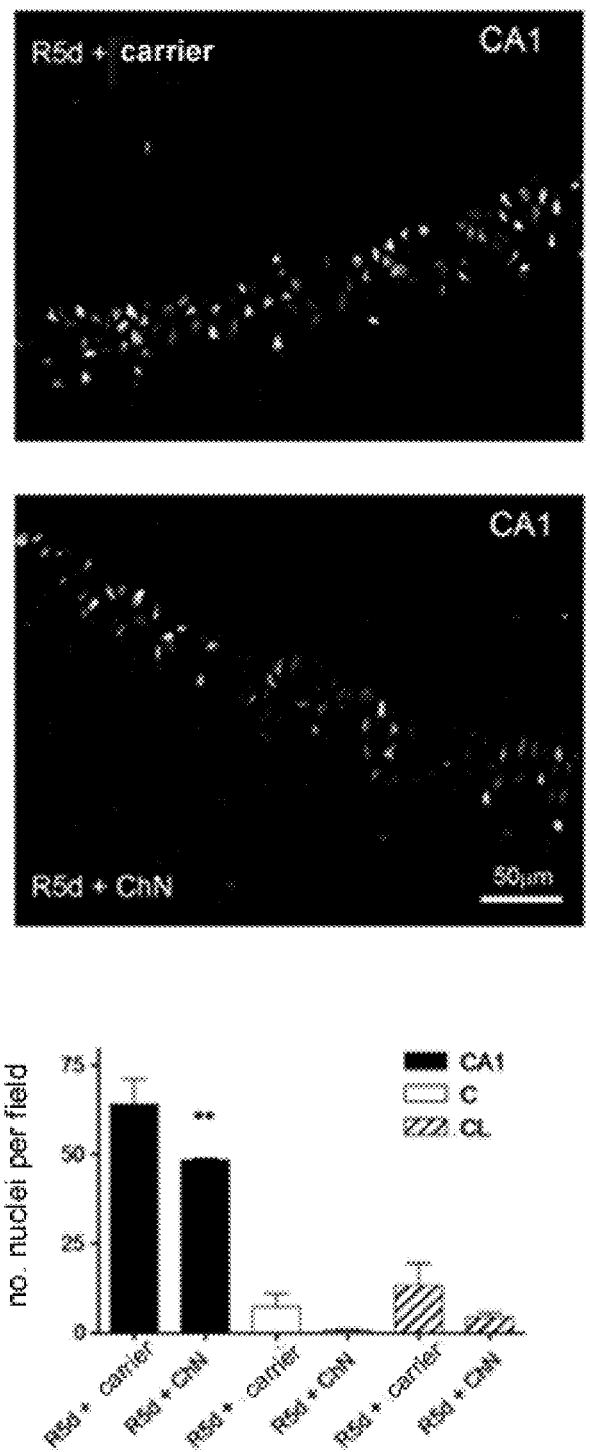
FIG. 4 shows how the brain sections of animals treated with carrier (R5d) showed a higher level of TUNEL-positive cells that the brain sections of animals treated with cholesteronitrone in CA1 region, cerebral cortex and lateral cortex. Therefore, the results showed that in animals treated with cholesteronitrone F2 the neuronal apoptotic death had significantly decreased in area CA1 5 days after reperfusion (R5d) (64.1±7.1 compared with 48.5±0.4 of nuclei per field, for animals treated with carrier and cholesteronitrone, respectively; ANOVA, p<0.0001; and p<0.01, according to post-Newman-Keuls test).
Figure 5:
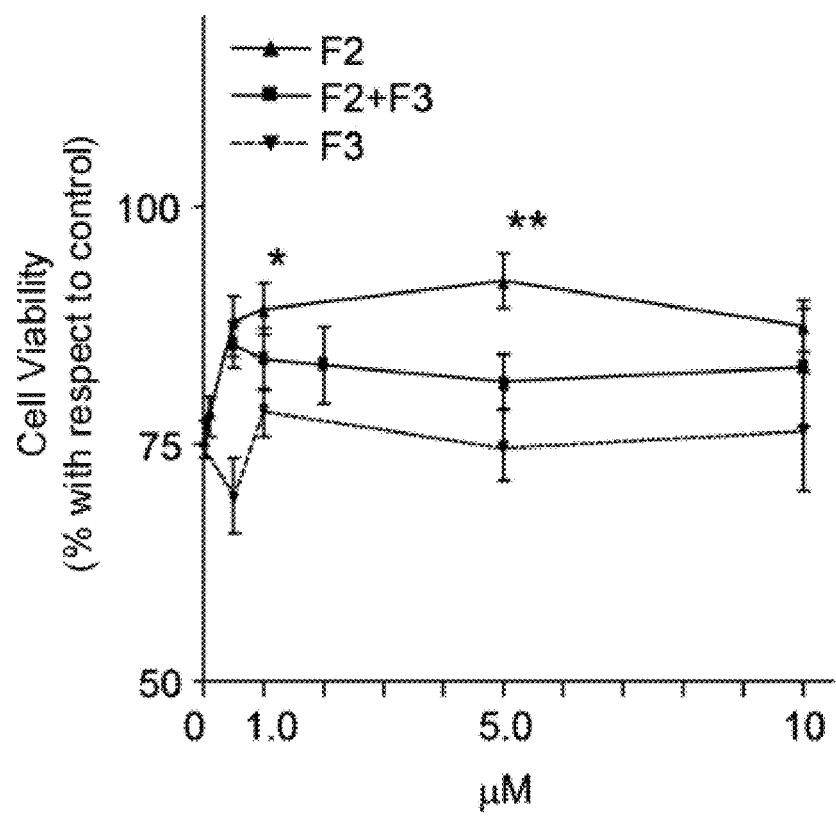
FIG. 5 shows neuronal viability in neuronal cultures exposed to OGD and treated with F2, F3 and a mixture of F2:F3 (at a 1:1 ratio, F2+F3) at the indicated concentrations. F2 and/or F3 was added at the beginning of the recovery period. Neuronal viability was evaluated 24 hours after recovery.

The induction of apoptosis was specifically demonstrated in the CA1 region in the R5d experiment with the TUNEL method (Ayuso M I, Martínez-Alonso E, Cid C, de Leciñana M A, Alcázar A. The translational repressor eIF4E-binding protein 2 (4E-BP2) correlates with selective delayed neuronal death after ischemia. *J Cereb Blood Flow Metab.* At press, doi: 10.1038/jcbfm.2013.60). Brain sections of animals treated with carrier (R5d) showed a higher level of TUNEL-positive cells than that of the animals treated with cholesteronitrone in the CA1 region, cerebral cortex and lateral cortex (FIG. 4). The results showed that in the animals treated with cholesteronitrone F2, neuronal apoptotic death dropped significantly in the CA1 area 5 days after reperfusion (R5d) (64.1±7.1 compared with 48.5±0.4 of nuclei per field, for animals treated with carrier and cholesteronitrone, respectively; ANOVA, $p<0.0001$; and $p<0.01$, according to the post-Newman-Keuls test) (FIG. 4, CA1). At the same time, the decrease in apoptotic cell death caused by cholesteronitrone was also observed in the cerebral cortex and lateral cortex, consistent with the results described above (7.2±3.8 and 1±0.5 of nuclei per field, for animals treated with carrier and cholesteronitrone, respectively, in the cerebral cortex; 13.3±6.2 and 4.3±1.4, for animals treated with carrier and cholesteronitrone, respectively, in the lateral cortex (FIG. 4).

In summary, it can be concluded that the pharmacological treatment of ischaemic animals with cholesteronitrone F2 at the concentrations at which it was proven to have a neuroprotective effect on neuronal cultures and on the CA1 region, significantly reduced apoptotic neuronal death in this area after ischaemic reperfusion.

The invention claimed is:

1. A method for inducing neuroprotection in a subject in need thereof, the method comprising administering to said subject a pharmaceutical composition comprising the compound -(E)-N-((8S,9SJORJ3RJ4SJ 7R)-I0,13-dimethyl-17-(R)-6-methylheptan-2-yl)-7,8,9, 11,12,13, 14,15, 16,17-decahydro-1H-cyclopenta[a]phenanthren-3(2H,6HJOH)-ylidene)methanamine oxide (F2) or a pharmaceutically acceptable salt or hydrate thereof, wherein the subject is suffering from ischemia or ischemic reperfusion.

2. The method according to claim 1, wherein the composition further comprises the compound —(Z)—N-((8S,9S, IOR, I3R, I4S,17R)-10, 13-dimethyl-17-(R)-6-methylheptan-2-yl)-7,8,9,11, 12,13, 14,15, 16,1 7-decahydro-1H-cyclopenta[a]phenanthren-3(2H,6H,10H)-ylidene)methanamine oxide (F3), or a pharmaceutically acceptable hydrate or salt thereof.

3. A method for inducing neuroprotection in a subject in need thereof, the method comprising administering to said subject a composition comprising the compound -(E)-N-((8S,9S, I OR, I3R, 1 4S, 1 7R)-I 0, 13-dimethyl-17-((R)-6-methylheptan-2-yl)-7, 8,9, 11,12,13, 14,15, 16,17-decahydro-1H-cyclopenta[a]phenanthren-3(2H,6HJOH)-ylidene)methanamine oxide (F2) or a pharmaceutically acceptable hydrate or salt thereof, wherein said composition is administered to said subject as an adjuvant therapy in combination with or instead of a first-line therapy suitable for preventing and/or treating a neurological disease, wherein the neurological disease is ischemia or ischemic reperfusion.

4. The method according to claim 3, wherein the first-line therapy comprises administering a thrombolytic agent to the subject.

5. The method according to claim 4, wherein said thrombolytic agent is tissue plasminogen activator (t-PA).

6. The method according to claim 5, wherein said tissue plasminogen activator (t-PA) is a recombinant tissue plasminogen activator (rt-PA).

7. The method according to claim 3, wherein the composition further comprises the compound —(Z)—N-((8S,9S, 10R,13R,14S, 17R)-10,13-dimethyl-17-(R)-6-methylheptan-2-yl)-7,8,9,11, 12,13, 14,15, 16,17-decahydro-1H-cyclopenta[a]phenanthren-3(2H,6H,10H)-ylidene) methanamine oxide (F3), or a pharmaceutically acceptable hydrate or salt thereof.

8. A method for treating a neurological disease in a subject in need thereof, the method comprising administering to said subject a pharmaceutical composition comprising the compound -(E)-N-((8S,9S,10R,13R,14S,17R)-10,13-dimethyl-17-((R)-6-methylheptan-2-yl)-7,8,9,11, 12,13, 14,15, 16,17-decahydro-1H-cyclopenta[a]phenanthren-3(2H,6H,10H)-ylidene)methanamine oxide (F2) or a pharmaceutically acceptable salt or hydrate thereof;
wherein said neurological disease is selected from the group consisting of ischemia and ischemic reperfusion.

9. The method according to claim 8, wherein the composition further comprises the compound —(Z)—N-((8S,9S, 10R,13R,14S, 17R)-10,13-dimethyl-17-(R)-6-methylheptan-2-yl)-7,8,9,11, 12,13, 14,15, 16,17-decahydro-1H-cyclopenta[a]phenanthren-3(2H,6H,10H)-ylidene) methanamine oxide (F3), or a pharmaceutically acceptable hydrate or salt thereof.

10. A method for treating a neurological disease in a subject in need thereof, the method comprising administering to said subject a composition comprising the compound -(E)-N-((8S,9S, 1OR, 13R, 14S,17R)-10, 13-dimethyl-17-((R)-6-methylheptan-2-yl)-7, 8,9,11, 12,13, 14,15, 16,17-decahydro-1H-cyclopenta[a]phenanthren-3(2H,6H,10H)-ylidene)methanamine oxide (F2), or a pharmaceutically acceptable hydrate or salt thereof;
wherein said neurological disease is selected from the group consisting of ischemia and ischemic reperfusion; and
wherein said composition is administered to said subject as an adjuvant therapy in combination with or instead of a first-line therapy suitable for treating said neurological disease.

11. The method according to claim 10, wherein the composition further comprises the compound —(Z)—N-((8S,9S,10R,13R,14S, 17R)-10,13-dimethyl-17-(R)-6-methylheptan-2-yl)-7,8,9,11, 12,13, 14,15, 16,1 7-decahydro-1H-cyclopenta[a]phenanthren-3(2H,6H,10H)-ylidene) methanamine oxide (F3), or a pharmaceutically acceptable hydrate or salt thereof.

12. The method according to claim 10, wherein the first-line therapy comprises administering a thrombolytic agent to the subject.

13. The method according to claim 12, wherein said thrombolytic agent is tissue plasminogen activator (t-PA).

14. The method according to claim 13, wherein said tissue plasminogen activator (t-PA) is a recombinant tissue plasminogen activator (rt-PA).

* * * * *